United States Patent [19]
Parsy et al.

[11] Patent Number: 5,089,546
[45] Date of Patent: Feb. 18, 1992

[54] OLIGOMER DERIVED FROM A POLYETHOXYLATED FATTY AMINE, PROCESS FOR PRODUCING SAME, AND ITS USE TO MODIFY THE SURFACE PROPERTIES OF POLYMERS

[75] Inventors: Roland Parsy, Le Havre; Daniel Augustin, Bernay; Christian Collette, Paris, all of France

[73] Assignee: Atochem, Paris, France

[21] Appl. No.: 567,773

[22] Filed: Aug. 15, 1990

Related U.S. Application Data

[62] Division of Ser. No. 335,736, Apr. 10, 1989, Pat. No. 4,980,438.

[30] Foreign Application Priority Data

Apr. 29, 1988 [FR] France .................. 88 05801

[51] Int. Cl.$^5$ ................................ C08F 20/36
[52] U.S. Cl. ................... 524/198; 526/310; 560/160; 560/196
[58] Field of Search .......... 526/310; 560/160, 196; 524/198

Primary Examiner—Joseph L. Schofer
Assistant Examiner—Jeffrey T. Smith
Attorney, Agent, or Firm—Sigalos & Levine

[57] ABSTRACT

An oligomer of the formula $$\begin{array}{c} (CR_1-CH_2)_a \\ | \\ O=C+O-C_2H_4-NH-C)_b-(O-C_2H_4)_n-N-R_2+Z)_{\overline{m}}R_3 \\ \phantom{O=C+O-C_2H_4-NH-}\|\phantom{)_b-(O-C_2H_4)_n-}| \\ \phantom{O=C+O-C_2H_4-NH-}O\phantom{)_b-(O-C_2H_4)_n-}(C_2H_4-O)_{n'}-H \end{array}$$

in which
$R_1 = H$ or $CH_3$;
$R_2 = C_tH_{2t}$ in whcih $0 \leq t \leq 18$;
$Z$ is selected from $C_2H_4$, $C2H2$ and $$\begin{array}{c} CH-CH_2 \\ | \\ S-C_2H_4-C_dF_{2d-1} \end{array}$$

in which $2 \leq d \leq 16$;
m is an integer such that $1 \leq m \leq 3$;
$R_3 = C_{t'}H_{2t'+1}$ in which $t' \geq 1$ and $8 \leq t+t'+2m \leq 22$
n and n' are identical or different integers, such that $2 \leq n+n' \leq 20$;
b is an integer equal to 0 or 1; and
a is an integer ranging from 2 to 500.

The invention also comprises the method of making the oligomer and thermoplastic films containing the same as well as the resultant thermoplastic films.

8 Claims, No Drawings

OLIGOMER DERIVED FROM A POLYETHOXYLATED FATTY AMINE, PROCESS FOR PRODUCING SAME, AND ITS USE TO MODIFY THE SURFACE PROPERTIES OF POLYMERS

This application is a division, of application Ser. No. 335,736, filed Apr. 10, 1989 now U.S. Pat. No. 4,980,438.

BACKGROUND OF THE INVENTION

The present invention pertains to a new oligomer derived from a polyethoxylated fatty amine. This oligomer possessing surface-active properties is mainly used to modify the surface properties of polymers and is more particularly used as an antifogging agent. It is produced by polymerizing a monomer obtained by the condensation or the addition of a polyethoxylated fatty amine with an acrylically or methacrylically unsaturated monomer.

It is known that the surface properties of a polymer can be modified by combining it with a surface-active micromolecule. It is, thus, possible to confer an antistatic or antifogging character on the polymer. In the latter case, the surface-active micromolecules are, e.g., a pentaerythritol monostearate as claimed in Japanese Patent No. 72.52156, a sorbitan monopalmitate as claimed in Japanese Patent No. 57.123239 or even a fluorinated or silicone-type surface-active agent as claimed in Japanese Patent Nos. 57.192445 and 58.76440. The introduction of these surface-active micromolecules into the polymers involves the disadvantage of leading to compositions that are unstable in the presence of moisture. These water-soluble surface-active agents are extracted by the water of condensation, so that their efficiency is very limited over time.

SUMMARY OF THE INVENTION

The oligomer according to the present invention, being a surface-active agent, permits this disadvantage of limited efficacy to be avoided.

Briefly, the present invention comprises oligomers of the formula:

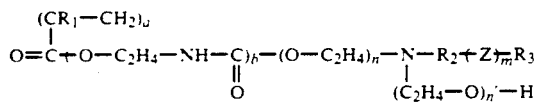

in which:
$R_1 = H$ or $CH_3$;
$R_2 = C_tH_{2t}$ in which $0 \leq t \leq 18$;
Z is selected from $C_2H_4$, $C_2H_2$ and

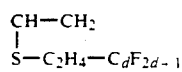

in which $2 \leq d \leq 16$;
m is an integer such that $1 \leq m \leq 3$;
$R_3 = C_{t'}H_{2t'-1}$ in which $t' \geq 1$ and $8 \leq t - t' + 2m \leq 22$;
n and n' are identical or different integers, such that $2 \leq n - n' \leq 20$;
b is an integer equal to 0 or 1; and
a is an integer ranging from 2 to 500, knowing that the oligomers preferably contain a majority of chains in which $5 \leq a \leq 100$.

The invention also comprises the process of making the oligomers as hereinafter set forth as well as thermoplastic polymer films resistant to fogging containing such oligomers.

DETAILED DESCRIPTION

This oligomer, added in an amount of 0.1 to 5, preferably 0.2 to 0.5, wt. % relative to the polymer, makes it possible to modify the surface properties of the polymer; in particular, it confers the antifogging property on it. This property is characterized by a modification of the process of water condensation on the polymer surface, such that the layer of water condensed will not diffuse light any more, or at least it will very substantially attenuate the diffusion of light. In addition, this oligomer, which is quasi nonextractable with water, leads to excellent stability over time of the desired properties of the polymer.

As was stated above, the surface-active oligomer is produced by polymerization of a monomer resulting from the condensation or the addition of a polyethoxylated fatty amine or a mixture of polyethoxylated fatty amines with an acrylically unsaturated monomer.

The polyethoxylated fatty amine is a derivative produced in the chemistry of fatty acids. Its production is well known in itself. It results from the addition of ethylene oxide to an amine as described in *Organic Chemistry*, Cram and Hammond, editors, McGraw Hill, page 214 (1959). This amine can be produced, e.g., according to the technique described in USSR Patent No. 598,876.

These polyethoxylated fatty amines used to produce the oligomer have the general formula

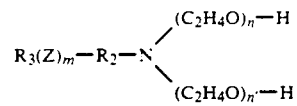

in which $R_2$, $R_3$, Z, n, n' and m are as defined above.

Industrially, these polyethoxylated fatty amines are formed by a mixture whose $R_3 (Z)_m R_2$ chains have a distribution centered around a principal value depending on the initial fat used to prepare the amine. Thus, the distribution characterizing the amines derived from coconut oil is centered around an alkyl chain containing 12 carbon atoms, whereas that characterizing the amines derived from tallow is centered around an alkylene chain containing 18 carbon atoms.

If the $R_3 (Z)_m R_2$ chain has at least one ethylenically unsaturated bond, it is possible to graft it with a fluorine-containing segment. The preferred mode of grafting consists of adding, in a free radical reaction, a fluorinated thiol of the general formula $C_dF_{2d-1}-C_2H_4-SH$, in which d has the meaning defined above. This fluorinated thiol is a product obtained by telomerization of tetrafluoroethylene, whose synthesis was described, e.g., in West German Patent No. 2,013,103. The radical addition of the fluorinated thiol consists of initiating the radical splitting of the thiol with a polymerization agent; the free radicals formed are added to the fatty amine to the ethylenic unsaturated bond before or after the ethoxylation. This addition is carried out in bulk or in a nonreactive solvent medium, while stirring.

under an inert atmosphere. The reaction temperature, which depends on the kinetics of decomposition of the polymerization agent, may range from 60° C. to 140° C.

The precursor of the surface-active oligomer is a monomer that can be subjected to free radical polymerization and has the formula:

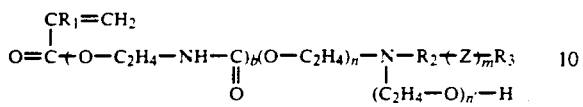

in which $R_1$, $R_2$, $R_3$, Z, b, m, n and n' have the meanings defined above.

This monomer is obtained:

(i) either by condensing a polyethoxylated fatty amine or a mixture of polyethoxylated fatty amines with acrylic or methacrylic acid or one of their derivatives such as acryloyl chloride, methyl acrylate or methyl methacrylate, or (ii) by addition of a polyethoxylated fatty amine or a mixture of polyethoxylated fatty amines with the 2-isocyanatoethyl acrylate or methacrylate of the formula

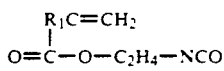

The condensation is preferably carried out in a solvent medium, while stirring, under an inert atmosphere, at a temperature sufficient to permit the elimination of the condensation product. It is possible to add to the reaction medium a condensation catalyst such as p-toluenesulfonic acid or zirconium tetrabutylate in the case of condensation with acrylic acid or methacrylic acid.

It is also possible to add a polymerization inhibitor, such as methyl hydroquinone, to the reaction medium to prevent any polymerization of the acrylate or methacrylate functional groups during the condensation. The progression of this condensation is measured by determining the hydroxyl functional groups of the polyethoxylated fatty amine.

The reaction is stopped when the amount of hydroxyl functional groups determined is equal to half the initial amount of hydroxyl functional groups. Statistically, one molecule of polyethoxylated fatty amine can be considered to bear one acrylate or methacrylate group in the monomer.

The addition is preferably carried out in a solvent medium, while stirring, under inert atmosphere, at a temperature between 30° C. and 90° C., preferably between 40° C. and 60° C. To increase the reaction rate, it is possible to add to the reaction medium a catalyst that is commonly used to produce polyurethanes, such as dibutyltin dilaurate. It is also possible to add to the reaction medium a polymerization inhibitor, just as in the case of the condensation. The addition reaction is checked by determining the hydroxyl functional groups and is stopped when the amount determined corresponds to half the initial amount of hydroxyl functional groups. Statistically, one molecule of the polyethoxylated fatty amine monomer can be considered to contain one acrylate or methacrylate functional group.

The oligomer according to the present invention is produced by free radical polymerization of the above-described monomer. The free radical polymerization of monomers is known. However, the free radical polymerization is carried out in a solvent medium, while stirring, under an inert atmosphere, in the presence of a polymerization agent, such as azobisisobutyronitrile or di-tert-butyl peroxide. The reaction temperature depends on the kinetics of decomposition of the polymerization agent; it may range from 40° C. to 130° C.

Since the polyethoxylated fatty amine used to produce the monomer can be a mixture of fatty amines with the different degrees of polyethoxylation, it is not ruled out that the final oligomer will be a mixture of oligomers, but it will correspond to the above-described formula.

The surface-active oligomer is incorporated in the thermoplastic polymers whose surface properties must be modified by any means available. The incorporation is usually carried out by mixing the oligomer with the polymer, preferably in the molten state.

The oligomer may be combined with any thermoplastic polymer, it being understood that as used herein the term "thermoplastic polymers" include not only the homopolymers, but also the thermoplastic copolymers or the mixtures of the thermoplastic polymers and/or copolymers. The oligomer may be combined, among other things, with polyethylene, polyvinyl chloride and even ethylene-vinyl acetate copolymers.

The polymer to which the oligomer is added can subsequently be transformed into thermoplastic polymer products according to any usual technique. The modification of the surface properties of the thermoplastic polymer products is evaluated in the examples below by determining the improvement of the antifogging behavior brought about by the surface-active oligomer.

This evaluation is carried out according to various techniques:

Hot Test

A thermoplastic polymer film is stretched horizontally 5 cm above a container of boiling water. The different phases are observed chronologically: appearance of diffusing droplets of fog, appearance of larger drops which drop off and are renewed and appearance of a continuous film of water. The most effective antifogging behavior is that which facilitates the rapid appearance of a continuous film of water that no longer diffuses light. This property is particularly desirable in the case of films for greenhouses, since the diffusion of light reduces the fraction of light received by the plants, which is harmful for their growth.

Cold Test

Containers of water, which are closed by a stretched film of thermoplastic polymer, are placed into a freezer having a temperature of $-18°$ C. The different phases during freezing are observed chronologically. These containers are exposed to $-18°$ C. for 20 hours, after which they are removed from the freezer. The different phases of warming are observed chronologically. In this cold test, an effective antifogging behavior is manifested by the formation of a continuous film of water.

Measurement of the Adhesion Tensions

These measurements are carried out on an average thermoplastic polymer film surface area of 2 $cm^2$ by soaking in water. The adhesion tension during the advancement ($T_A$) of the film in the water and the adhesion tension on withdrawal ($T_R$) of the film are determined. The difference between these two tensions, $\Delta W_{SL} = T_A - T_R$, represents the wetting hysteresis. These values are expressed in millinewtons per meter (mN/m).

The surface tension of the water after this soaking is also measured. If this surface tension ($\gamma_L$) is lower than that of pure water, 72 mN/m, it means that part of the antifogging agent has migrated into the water during the soaking; this migration is detrimental to the long-term effectiveness of this anti fogging agent. The low solubility in water of the surface-active oligomer is manifested by a quasi negligible change in the surface tension of the water after soaking.

Condensation Kinetics

A water container is closed with a stretched thermoplastic film and is held at 33° C. The water vapor condensation phenomenon is monitored by optical microscopy (magnification: 250). The kinetics of droplet coalescence leading to the formation of a continuous film of water are observed.

It is apparent from all the evaluations that the surface-active oligomer induces an antifogging behavior that is at least comparable to that of the commercially available antifogging agents, such as ATMER ®. The value of this surface-active oligomer is, contrary to the commercially available antifogging agents, the quasi complete absence of extraction by the condensed water. Unlike the efficacy over time of the oligomer, the efficacy over time of the commercially available agents is limited due to continuous extraction.

The present invention will be further described by, but not limited to, the following examples which are set forth for purposes of illustration only.

EXAMPLE 1

300 g of NORAMOX 05 ®, which is a polyethoxylated fatty amine whose fatty chain $R_3$ $(Z)_m$ $R_2$ is mainly an oleyl repeat unit, in which $R_3$ is a $CH_3(CH_2)_7$ group, Z is a $CH=CH$ group, $R_2$ is a $(CH_2)_8$ group and the number of ethoxylated repeat units $(n-n')$ equals 5, are charged into a two-liter three-necked reaction vessel. The hydroxyl number of this product is 262.5. 90.94 g of acrylic acid, 2.7 g of p-toluenesulfonic acid, 0.6 g of hydroquinone and 1,200 cc of toluene are added to the NORAMOX 05 ® in the reaction vessel. The entire mixture is refluxed while stirring and under nitrogen. The acid number is periodically determined. The reaction is stopped when the acid number is close to the theoretical number corresponding to the monoesterification of the polyethoxylated fatty amine. The solvent is removed by distillation under low vacuum, and the residual acrylic acid is removed at 150° C. under a vacuum of 110 Pa. The hydroxyl number of the product obtained is 144.8.

328 g of the product obtained, 6 g of azobisisobutyronitrile and 600 cc of ethyl alcohol are charged into a two-liter three-necked reaction vessel. The entire mixture is held at 72° C. for six hours while stirring under an inert atmosphere. The ethanol is subsequently distilled off first under a low vacuum at 80° C. and then for ten minutes at 150° C. under a vacuum of 66 Pa.

The product according to the present invention is recovered and its composition is evaluated by gel permeation chromatography, using polystyrene for calibration. The product is formed by acryl chains whose molecular weights, represented by the values of "a", are between 4 and 25, and most of them are centered around 4 and 7.

EXAMPLE 2

200 g of NORAMOX 05 ®, 468.5 g of fluorinated thiol of the formula $C_6F_{13}-C_2H_4-SH$ and 4.84 g of azobisisobutyronitrile are charged into a one-liter reaction vessel. The entire mixture is held for seven hours at 77° C. under a nitrogen atmosphere while stirring. The excess fluorinated thiol is then distilled off at 130° C. under low vacuum. The yield of grafting of the fluorinated thiol to the unsaturated bond of the polyethoxylated fatty amine is 92.8%. The hydroxyl number of the amine obtained is 150.

300 g of the above-described grafted amine, 46.3 g of acrylic acid, 1.53 g of p-toluenesulfonic acid, 0.6 g of hydroquinone and 1,200 cc of toluene are charged into a two-liter three-necked reaction vessel. The entire mixture is refluxed while passing through nitrogen and stirring. The acid number is periodically determined. The reaction is stopped after refluxing for 19 hours. The toluene and the residual acrylic acid are extracted by vacuum distillation under a vacuum of 110 Pa. The hydroxyl number of the product obtained is 79.8.

302 g of the monomer obtained, 6 g of azobisisobutyronitrile and 600 cc of ethanol are charged into a two-liter three-necked reaction vessel. The mixture is held at 70° C. for six hours while stirring and under nitrogen. Two g of azobisisobutyronitrile are then charged in, and the polymerization is continued for four hours at 70° C. The ethanol is subsequently removed by distillation.

The product is analyzed under the conditions described in Example 1. It is formed by acryl chains whose weights correspond to the "a" values ranging from 4 to 63 and mainly centered around 4 and 10.

EXAMPLE 3

Using an extruder (model BUSS PR46), an ethylene-vinyl acetate copolymer (1020 VN3 from ATOCHEM) is mixed and granulated with 5,000 ppm of the oligomer from Example 1. The mixing temperature is 175°–190° C. for a flow rate of 20 kg/hour. 20 kg of granular product thus prepared are extruded in the form of a sheet with a width of 500 mm, using a TROESTER extruder equipped with a mixing tip and a GLOENCO die with a diameter of 100 mm. The extrusion temperatures range from 140° C. to 160° C. The speed of rotation of the extruder screw and the speed of rotation of the extruder screw and the speed of sheet drawing are adjusted such that the sheet is formed of a film with a thickness of 100 microns (Specimen 2).

A control experiment is carried out under the same conditions without adding oligomer (Specimen 1).

An experiment is carried out under the above-described conditions, granulating the polyethylene with 5,000 ppm of the oligomer from Example 2 (Specimen 3).

Evaluation of Antifogging Properties: Hot Test and Cold Test

Films cut from Specimens 1, 2 and 3 are stretched horizontally 5 cm above a container of boiling water.

Instantaneous appearance of fog is observed in the case of Specimen 1; this is followed by the appearance of fine droplets after an exposure time of 32 seconds and then the appearance of drops after 5 minutes 50 seconds.

The large drops fall off the film after 25 minutes, and condensation begins again.

In the case of Specimen 2, appearance of fine droplets is seen after an exposure time of 30 seconds; drops appear after 1 minute 25 seconds. After 2 minutes 50 seconds, the drops gather to form a continuous sheet of water which does not diffuse light.

Almost instantaneous formation of a continuous sheet of water is seen in the case of Specimen 3.

Containers placed in a freezer with a temperature of −18° C. are sealed with films of Specimens 1, 2 and 3.

Fog is formed instantaneously in the case of Specimen 1, and fine droplets are formed after seven minutes, and finally, droplets after cooling for 18 minutes.

The same phenomena are observed in the case of Specimen 2, but the fine droplets only appear after six minutes and drops after 15 minutes.

Formation of a very thin layer of fog is observed in the case of Specimen 3, and it gives way to a continuous film of water after two minutes of cooling.

The containers are held at −18° C. for 20 hours and then they are allowed to reach room temperature.

In the case of Specimen 1, appearance of drops on the inner face of the film and the presence of fog on the external face are seen after ten minutes.

Appearance of drops on the inner face of the film and of fine droplets on the external face is seen after ten minutes in the case of Specimen 2; on the whole, the film diffuses light less markedly than Specimen 1.

The film remains constantly transparent in the case of Specimen 3.

EXAMPLE 4

Granular ethylene-vinyl acetate copolymer (1005 VL4 from ATOCHEM) containing 5,000 ppm of the oligomer according to Example 1 is produced under the conditions described in Example 3.

20 kg of granular material produced are extruded in the form of a sheet with a width of 350 mm, using a KAUFMAN PKH 28-65 extruder equipped with a mixing tip. The temperature of the material is 210° C. The speed of rotation of the extruder screw and the rate of swelling of the sheet are adjusted such that the thickness of the sheet will be 150 microns (Specimen 5).

A control experiment is carried out under the same conditions without adding oligomer (Specimen 4).

An experiment is carried out under the same conditions as above, granulating the copolymer with 5,000 ppm of oligomer from Example 2 (Specimen 6).

An experiment is carried out under the same conditions as above, granulating the copolymer with 5,000 ppm of ATMER 184 ®, a product commercially available as an antifogging agent (Specimen 7).

A comparative experiment is carried out under the same conditions as above, granulating the copolymer with 5,000 ppm of NORAMOX 05 ® (Specimen 8).

Evaluation of the Antifogging Properties

Films cut out of Specimens 4, 5, 6 and 8 are stretched horizontally 5 cm above a container of boiling water.

Instantaneous fogging is seen in the case of Specimen 4; this is followed by the formation of fine droplets after exposure for 50 seconds, and finally, drops after exposure for 5 minutes 40 seconds. The drops fall off after ten minutes, and the condensation cycle starts again.

In the case of Specimen 5, the appearance of fine droplets is seen after exposure for 15 seconds, and then drops are seen after 2 minutes 50 seconds; the drops spread out to form a continuous film of water.

The same phenomena are observed in the case of Specimens 6 and 8, except that drops are formed after 2 minutes 30 seconds and 4 minutes, respectively.

Condensation Kinetics

The condensation kinetics were measured under an optical microscope.

The containers of water maintained at 33° C. are sealed by films cut out of Specimens 4, 5, 6, 7 and 8. The form in which the water condenses is observed after exposure for 15 seconds, as well as 5, 15 and 60 minutes. The observations are shown in the table below; the term "puddle" designates a spread-out drop of water with slight diffusion, with irregular contours, contrary to the contours of drops, which are circular. The forms of condensation are identical on the two faces of the film except in the case of Specimen 8, which shows asymmetry.

Only Specimens 5, 6 and 7 have interesting antifogging behavior.

|  | Forms of condensation observed after | | | |
|---|---|---|---|---|
|  | 15 seconds | 5 minutes | 15 minutes | 60 minutes |
| SPECIMEN 4 | 2-micron droplets | 8-micron droplets | 15–20-micron droplets | 60–70-micron droplets |
| SPECIMEN 5 | 1–2-micron droplets | 20-micron "puddles" | Ca. 60–80-micron "puddles" | Nondiffusing merging "puddles" |
| SPECIMEN 6 | Less-than-1-micron droplets | 40–60-micron "puddles" | Nondiffusing merging "puddles" of ca. 120 microns | Nondiffusing merging "puddles" |
| SPECIMEN 7 | Less-than-1-micron droplets | 40–60-micron "puddles" | Nondiffusing merging "puddles" of ca. 120 microns | Nondiffusing merging "puddles" |
| SPECIMEN 8 First Face | 1–2-micron droplets | 4–8-micron droplets | 12–16 micron "puddles" | 40–60 micron "puddles" |
| SPECIMEN 8 Second Face | 1–2-micron droplets | 4–8-micron droplets | 8–12 micron droplets | 16–20 micron droplets |

Evaluation of Water Resistance

The long-term efficacy of an antifogging additive is linked with the fact that it is entrained and dissolved by the water of condensation only slightly at best.

This efficacy can be evaluated according to the following method: The adhesion tension T of a film doped with an antifogging agent is measured in twice-distilled water, after which the surface tension $\gamma_L$ of this water is measured according to the hoop method: the higher the water extractability of the additive, the lower the surface tension of the water below its initial value (72 mN/m).

The measurement of the adhesion tension is carried out according to the experimental protocol described by T. and L. Guastalla (*Journal de Chimie Physique* 49(5) (1951) and 51(10) (1954), using a LAUDA automatic tensiometer.

The hoop test is carried out according to DIN standard No. 53194.

The results obtained for Specimens 4 through 7 are shown in the table below: $T_A$ and $T_R$ are the adhesion tensions on advancement and withdrawal, and $\gamma_L$ is the surface tension of water after this wetting cycle.

|  | $T_A$, mN/m* | $T_R$, mN/m* | $\gamma_L$, mN/m* |
|---|---|---|---|
| SPECIMEN 4 | −22 | 8 | 72 |
| SPECIMEN 5 | −16 | 6 | 71 |
| SPECIMEN 6 | −14 | 11 | 72 |
| SPECIMEN 7 | 8 | 22 | 60 |

*mN/m = millinewtons per meter

It is seen that the surface tension of twice-distilled water changes only slightly at best ($\gamma_L = 72$ mN/m) for Specimens 4, 5 and 6, whereas it drops to 60 mN/m in the case of the specimen doped with ATMER 184 ®.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. The process for making antifogging thermoplastic polymer films comprising admixing an oligomer or a mixture of oligomers with a thermoplastic resin and then forming said admixture into a film, the oligomer or mixture of oligomers being present in an amount sufficient to impart antifogging properties to said film and such oligomer or mixture of oligomers having the formula:

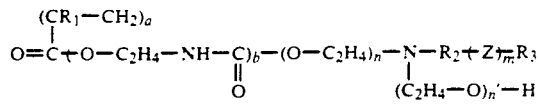

in which
$R_1 =$ H or $CH_3$;
$R_2 = C_tH_{2t}$ in which $0 \leq t \leq 18$;
Z is selected from $C_2H_4$, $C_2H_2$ and

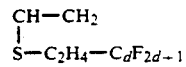

in which $2 \leq d \leq 16$;
m is an integer such that $1 \leq m \leq 3$;
$R_3 = C_{t'}H_{2t'+1}$ in which $t' \geq 1$ and $8 \leq t+t'+2m \leq 22$
n and n' are identical or different integers, such that $2 \leq n+n' \leq 20$;
b is an integer equal to 0 or 1; and
a is an integer ranging from 2 to 500.

2. The process of claim 1 in which the film contains from about 0.1 to 5 wt. % oligomer or mixture of oligomers.

3. An antifogging thermoplastic film consisting essentially of a thermoplastic polymer and about 0.1 to 5 wt. % of an oligomer or mixture of such oligomers, relative to the polymer, said oligomer or mixture of oligomers having the formula:

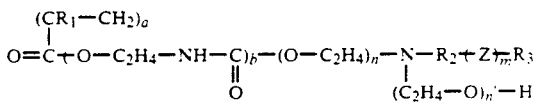

in which
$R_1 =$ H or $CH_3$;
$R_2 = C_tH_{2t}$ in which $0 \leq t \leq 18$;
Z is selected from $C_2H_4$, $C_2H_2$ and

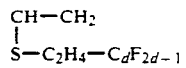

in which $2 \leq d \leq 16$;
m is an integer such that $1 \leq m \leq 3$;
$R_3 = C_{t'}H_{2t'+1}$ in which $t' \geq 1$ and $8 \leq t+t'+2m \leq 22$
n and n' are identical or different integers, such that $2 \leq n+n' \leq 20$;
b is an integer equal to 0 or 1; and
a is an integer ranging from 2 to 500.

4. The thermoplastic film of claim 3 wherein the thermoplastic polymer is polyethylene, polyvinyl chloride, or an ethylene-vinyl acetate copolymer.

5. The process of claim 1 wherein a majority of chains in the oligomer are such that $5 \leq a \leq 100$.

6. The process of any one of claims 1, 2 or 5, wherein a mixture of oligomers is used.

7. The thermoplastic film of claim 4 wherein a majority of chains in the oligomer are such that $5 \leq a \leq 100$.

8. The thermoplastic film of any one of claims 3, 4 or 7, wherein a mixture oligomers is used.

* * * * *